United States Patent [19]

Presson et al.

[11] 4,362,603

[45] Dec. 7, 1982

[54] CONTINUOUS ACETONITRILE RECOVERY PROCESS

[75] Inventors: Robert D. Presson, Bedford; Hsin-Chih Wu, Parma, both of Ohio; Edward J. Sockell, Port Lavaca, Tex.

[73] Assignee: The Standard Oil Company, Cleveland, Ohio

[21] Appl. No.: 222,196

[22] Filed: Jan. 2, 1981

[51] Int. Cl.³ .............................................. B01D 3/36
[52] U.S. Cl. ......................................... 203/75; 203/77; 203/78; 203/80; 203/82; 203/84; 203/DIG. 3; 203/94; 260/465.5 A

[58] Field of Search .......... 260/465.1, 465.3, 465.5 A, 260/465.9; 203/12, 14, 71, 73, 75, 77, 78, 80, 82, 84, 91, 94, 98, DIG. 3

[56] References Cited

U.S. PATENT DOCUMENTS 3,264,197 8/1966 Schönbeck et al. .......... 203/DIG. 3

Primary Examiner—Frank Sever
Attorney, Agent, or Firm—J. E. Miller, Jr.; H. D. Knudsen; L. W. Evans

[57] ABSTRACT

Crude acetonitrile is purifed to 99+ weight percent by a continuous distillation procedure.

12 Claims, 1 Drawing Figure

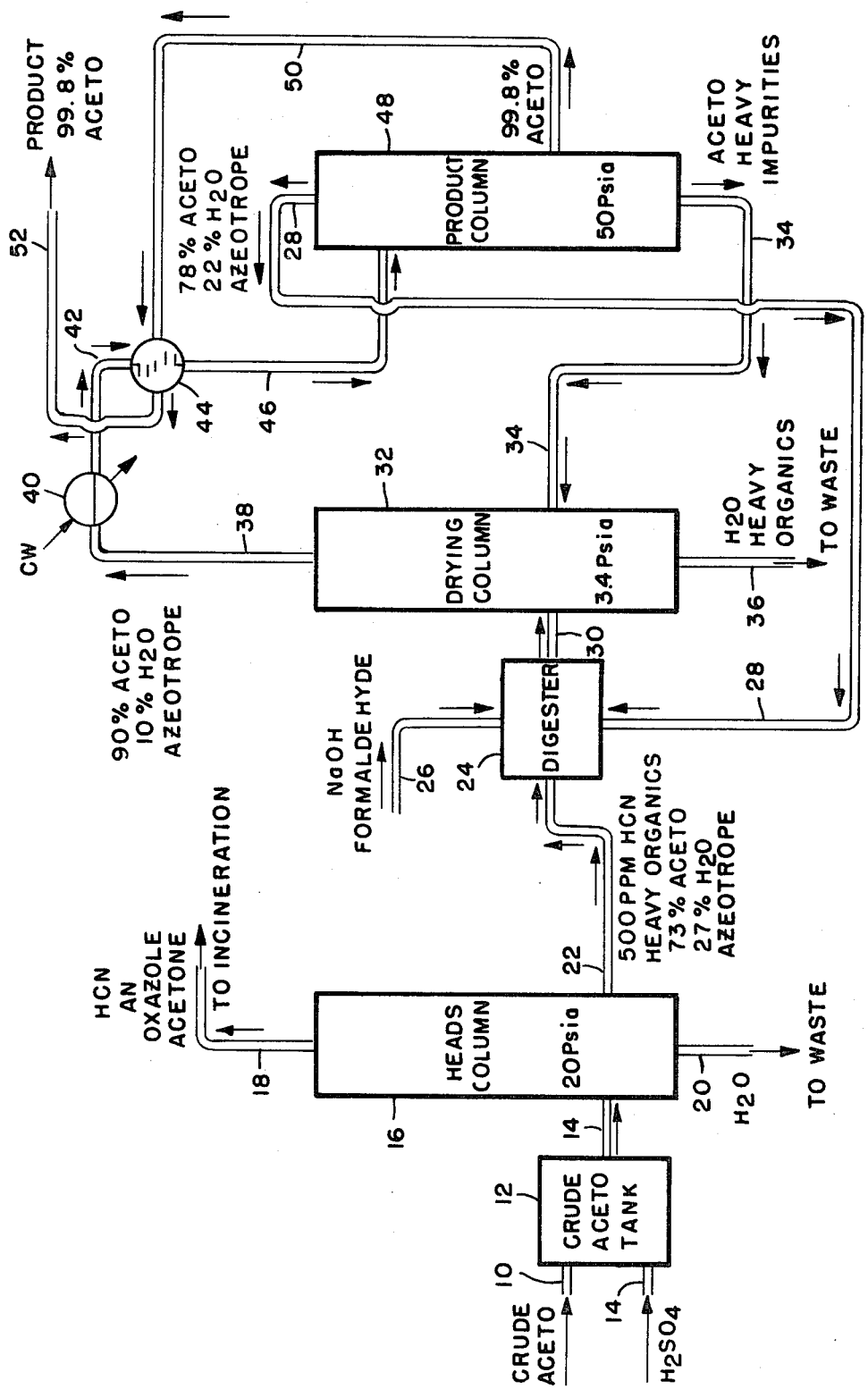

CONTINUOUS ACETONITRILE RECOVERY PROCESS

BACKGROUND OF THE INVENTION

In the production of acrylonitrile by the catalytic ammoxidation of propylene with ammonia and oxygen, a crude acetonitrile byproduct is produced. This material normally is composed of, on a weight basis, about 52% acetonitrile, 43.6% water, 2.5% HCN, 0.5% acrylonitrile and 1.3% other organics such as oxazole, allyl alcohol, acetone and propionitrile.

Traditionally, this crude acetonitrile byproduct has simply been disposed of by incineration. More recently, however, it has been processed so as to recover acetonitrile as a valuable byproduct.

In this processing, the crude acetonitrile is first distilled to drive off HCN. Then, the HCN-free material is distilled to produce an acetonitrile/water azeotrope containing about 25% water, which in turn is then slurried with anhydrous calcium chloride. The anhydrous calcium chloride takes up most of the water in the azeotrope to produce an acetonitrile/water mixture containing about 3% to 5% water, which in turn is distilled to produce a pure acetonitrile product.

The conventional process for recovering the acetonitrile produces a relatively large amount of waste calcium chloride which must be disposed of and further is accomplished in a batch operation which leads to various operational difficulties.

Accordingly, it is an object of the present invention to provide a new technique for recovering acetonitrile from a crude acetonitrile process stream which is simple and straightforward to carry out and can be conducted on a continuous basis.

SUMMARY OF THE INVENTION

This and other objects are accomplished by the present invention, which is based on the discovery that acetonitrile in 99+% purity can be recovered by a continuous distillation procedure carried out in three stages at three different pressures.

Accordingly, the present invention provides a novel technique for continuously recovering highly pure acetonitrile from crude acetonitrile containing acetonitrile, water, HCN and heavy organics, the process comprising:

(1) distilling the crude acetonitrile in a first distillation zone at a first pressure at or above 1 atmosphere to remove HCN therefrom and produce a first acetonitrile/water azeotrope and a first bottoms product containing water, (2) distilling the first azeotrope in a second distillation zone at a second pressure less than 1 atmosphere to separate the first azeotrope into a second bottoms product containing water and a second acetonitrile/water azeotrope having a greater acetonitrile concentration than the first azeotrope, and (3) distilling the second acetonitrile/water azeotrope in a third distillation zone at a third pressure above the first pressure to produce a third acetonitrile/water azeotrope containing substantially all of the water in the second azeotrope, a third bottoms product comprising acetonitrile and heavy organics and a sidestream comprising the highly pure acetonitrile.

BRIEF DESCRIPTION OF THE DRAWING

The sole FIGURE is a schematic representation of the present invention.

DETAILED DESCRIPTION

In accordance with the present invention, crude acetonitrile is processed to recover highly pure acetonitrile as a valuable byproduct. By "highly pure" acetonitrile is meant acetonitrile having a purity of at least 95%. Normally, acetonitrile can be produced by the present invention with purities as high as 99.9%, the balance being water and extremely small amounts of organics. The crude acetonitrile which is processed in accordance with the present invention is any acetonitrile/water mixture containing at least 15% water. Thus, the inventive process is applicable in the processing of various water/acetonitrile azeotropes. The invention, however, finds broadest application in the processing of the crude acetonitrile streams produced by the ammoxidation of propylene with oxygen and ammonia to form acrylonitrile. As indicated above, such crude acetonitrile streams normally contain about 52% acetonitrile, 43.6% water, 0.5% acrylonitrile, 2.5% HCN and 1.3% other minor impurities such as oxazole, allyl alcohol, acetone and propionitrile.

Crude acetonitrile recovered from an acrylonitrile plant and having the above composition can be conveniently processed by the present invention in accordance with the flow scheme illustrated in the FIGURE. In accordance with this system, the crude acetonitrile is fed via inlet line 10 to a crude acetonitrile holding tank 12. Sulfuric acid is charged via line 14 into crude acetonitrile tank 12 to acidify the crude acetonitrile to a pH of about 7 to stabilize the cyanohydrins and neutralize free ammonia.

After acidification, the neutralized crude acetonitrile is charged via line 14 into heads column 16 wherein it is distilled at a pressure of about 18 psia to three phases. The light components in the crude acetonitrile, namely HCN, acrylonitrile, oxazole and acetone, are withdrawn from heads column 16 as a vapor draw and discharged to incineration via line 18. Water is recovered from the bottom of heads column 16 and discharged via line 20 to waste. A first acetonitrile/water azeotrope containing about 70% acetonitrile, 30% water, 500 ppm HCN and very small amounts of heavy organics is recovered as a side draw.

The first acetonitrile/water azeotrope is then transferred via line 22 to digester 24. An HCN digester comprising an aqueous solution of sodium hydroxide and formaldehyde is added via line 26 to digester 24 so that the HCN in the first azeotrope is destroyed. This technique of digesting HCN is more thoroughly described in commonly assigned application Ser. No. 102,088, filed Dec. 10, 1979, the disclosure of which is incorporated herein by reference. Into digester 24 via line 28 is also charged another acetonitrile/water azeotrope (third azeotrope), this azeotrope containing about 22% water.

The HCN-free acetonitrile/water mixture passing out of digester 24 is charged via line 30 into drying column 32. In addition, a stream comprising acetonitrile containing a small amount of heavy impurities is also charged into drying column 32 via line 34. In drying column 32, the acetonitrile/water mixture therein is distilled at a pressure below one atmosphere, e.g. 3.4 psia, to produce a bottoms product comprising water and heavy organics, which are discharged to waste via line 36, and a gaseous top draw comprising a second acetonitrile/water azeotrope, the second azeotrope containing about 10% water.

The second acetonitrile/water azeotrope is charged via line 38 into condenser 40 where it is condensed, passed via line 42 through heat exchanger 44 where it is heated, and then charged via line 46 into product column 48. In product column 48, the second acetonitrile/water azeotrope is distilled at high pressure, e.g. 50 psia, into three phases. A bottoms product comprising acetonitrile containing heavy impurities is withdrawn from the bottom of product column 48 and recycled via line 34 to drying column 32. A third acetonitrile/water azeotrope is withdrawn from the top of product column 48 and recycled via line 28 to digester 24 where it is mixed with the first acetonitrile/water azeotrope produced in heads column 16. Because product column 48 is operated at high pressure, all of the water in the second acetonitrile/water azeotrope charged into product column 48 is recovered in the overhead stream of product column 48, i.e. the third acetonitrile/water azeotrope, leaving high purity acetonitrile in the product column. This high purity acetonitrile (99.8 weight percent acetonitrile) is drawn off column 48 as a liquid sidestream via line 50, and after cooling in heat exchanger 44 is discharged as product via line 52.

From the above, it can be seen that the present invention very simply and easily produces high purity acetonitrile by distillation without using calcium chloride to remove water. Thus, waste disposal problems associated with the prior art techniques are largely eliminated.

Although only a single embodiment of the invention has been described above, many modifications can be made without departing from the spirit and scope of the invention. For example, instead of an aqueous solution of sodium hydroxide and formaldehyde, any other chemical which will destroy HCN without adversely affecting the acetonitrile product can be used as the HCN digester fed to digester 24. In addition, other pressures than those described above can be used in the three distillation columns of the invention. For example, the pressures in the heads column, drying column and product column can be 15 to 25 psia, 0.1 to 10 psia and 15 to 100 psia, respectively, with the pressure in the product column preferably being at least 5 psi greater than the pressure in the heads column. More preferably, the pressures in the heads, drying and product columns are 16 to 20 psia, 3 to 4 psia and 40 to 55 psia, respectively. All such modifications are intended to be included within the scope of the invention, which is to be limited only by the following claims.

We claim:

1. A continuous process for recovering highly pure acetonitrile from crude acetonitrile by-produced during amoxidation of propylene containing acetonitrile, water, HCN and heavy organics, said process comprising:
   (1) distilling said crude acetonitrile in a first distillation zone at a first pressure at or above 1 atmosphere to remove HCN therefrom and produce a first acetonitrile/water azeotrope and a first bottoms product containing water,
   (2) distilling said first azeotrope in a second distillation zone at a second pressure less than 1 atmosphere to separate said first azeotrope into a second bottoms product containing water and a second acetonitrile/water azeotrope having a greater acetonitrile concentration than said first azeotrope, and
   (3) distilling said second acetonitrile/water azeotrope in a third distillation zone at a third pressure above 1 atmosphere to produce a third acetonitrile/water azeotrope containing substantially all of the water in said second azeotrope, third bottoms product comprising acetonitrile and heavy organics and a sidestream comprising said highly pure acetonitrile of at least 95%.

2. The process of claim 1 further comprising recycling said third bottoms product to said second distillation zone.

3. The process of claim 2 further comprising recycling said third azeotrope to said second distillation zone.

4. The process of claim 3 wherein said third azeotrope is mixed with said first azeotrope prior to charging into said second distillation zone.

5. The process of claim 4 wherein an HCN digester is added to the mixture of said first azeotrope and third azeotrope prior to charging said mixture into said second distillation zone.

6. The process of claim 3 further comprising condensing said second azeotrope and thereafter heating the condensed second azeotrope prior to charging of said second azeotrope into said third distillation zone, said second azeotrope being heated by indirect heat exchange with said sidestream.

7. The process of claim 3 wherein said first pressure is about 15 to 25 psia, said second pressure is about 0.1 to 12 psia and said third pressure is about 15 to 100 psia.

8. The process of claim 7 wherein said third pressure is at least 5 psi greater than said first pressure.

9. The process of claim 8 wherein said first pressure is about 16 to 20 psia, said second pressure is about 3 to 4 psia and said third pressure is about 40 to 55 psia.

10. The process of claim 1 wherein said HCN is removed from said first distillation as an over-head stream and further wherein said first acetonitrile/water azeotrope is removed from said first distillation zone as a side stream.

11. The process of claim 10 wherein said crude acetonitrile is a by-product produced during the ammoxidation of propylene.

12. A process for recovering highly pure acetonitrile from a first acetonitrile/water mixture by-produced during amoxidation of propylene containing about 15 weight percent or more water comprising:
   (1) distilling said first mixture in a first distillation zone at a first pressure below 1 atmosphere to produce a water-containing bottoms product and a second acetonitrile/water mixture comprising an azeotrope of acetonitrile and water more concentrated in acetonitrile than said first mixture,
   (2) distilling said second mixture at a second pressure above 1 atmosphere to produce a third acetonitrile/water mixture comprising an azeotrope of acetonitrile and water less concentrated in acetonitrile than said second mixture and said highly pure acetonitrile of at least 95%, and
   (3) recycling said third mixture so that said third mixture is distilled along with said first mixture.

* * * * *